United States Patent

Ruka et al.

[11] Patent Number: 5,277,995
[45] Date of Patent: Jan. 11, 1994

[54] ELECTRODE AND METHOD OF INTERCONNECTION SINTERING ON AN ELECTRODE OF AN ELECTROCHEMICAL CELL

[75] Inventors: Roswell J. Ruka, Churchill Boro; Lewis J. H. Kuo, Monroeville, both of Pa.

[73] Assignee: Westinghouse Electric Corp., Pittsburgh, Pa.

[21] Appl. No.: 32,347

[22] Filed: Mar. 16, 1993

[51] Int. Cl.[5] .................... H01M 8/00; H01M 8/02
[52] U.S. Cl. ..................... 429/31; 29/623.5; 429/45; 427/115
[58] Field of Search .............. 429/30–33, 45, 218; 427/115, 126.1, 322.402; 264/61, 29/623.1, 623.5 623.5

[56] References Cited

U.S. PATENT DOCUMENTS

| | | | |
|---|---|---|---|
| 4,861,345 | 8/1989 | Bowker et al. | 429/31 X |
| 4,895,576 | 1/1990 | Pal et al. | 29/623.5 |
| 5,080,689 | 1/1992 | Pal et al. | 29/623.5 |

Primary Examiner—Anthony Skapars
Attorney, Agent, or Firm—Daniel P. Cillo

[57] ABSTRACT

An electrode structure (10) is made by applying a base layer of doped $LaCrO_3$ particles on a portion of an electrode (16) and then coating the particles with a top layer composition such as $CaO + Al_2O_3$, $SrO + Al_2O_3$, or $BaO + Al_2O_3$, and then heating the composition for a time effective to melt the composition and allow it to fill any open porosity in the base layer of doped $LaCrO_3$ to form an interconnection (26), after which solid oxide electrolyte (18) can be applied to the remaining portion of the electrode (16) and the electrolyte (18) can be covered with a cermet exterior electrode (20).

10 Claims, 1 Drawing Sheet

ELECTRODE AND METHOD OF INTERCONNECTION SINTERING ON AN ELECTRODE OF AN ELECTROCHEMICAL CELL

GOVERNMENT CONTRACT

The Government of the United States of America has rights in this invention pursuant to Contract No. DE-AC-0280-ET-17089, awarded by the U.S. Department of Energy.

BACKGROUND OF THE INVENTION

The present invention relates to a method of depositing an electronically conductive interconnection layer on an electrode of an electrochemical cell.

High temperature electrochemical cells are well known. In these types of cells, typified by fuel cells, a porous support tube of calcia stabilized zirconia, has an air electrode cathode deposited on it. The air electrode may be made of, for example, oxides of the perovskite family, such as doped lanthanum manganite. Surrounding the major portion of the outer periphery of the air electrode is a layer of gas-tight solid electrolyte, usually yttria stabilized zirconia. A selected radial segment of the air electrode is covered by an interconnection material. The interconnection material may be made of a doped lanthanum chromite film. The generally used dopant is Mg, although Ca and Sr have also been suggested.

Both the electrolyte and interconnect material are applied on top of the air electrode by a modified electro-chemical vapor deposition process, at temperatures of up to 1450° C., with the suggested use of vaporized halides of zirconium and yttrium for the electrolyte, and vaporized halides of lanthanum, chromium, and magnesium, or calcium or strontium for the interconnection material.

It would be economically desirable to form at least the interconnect material by a simple sintering process which would employ less expensive equipment and use low cost oxides or chemicals to form the desired interconnection.

In U.S. Pat. No. 4,631,238 (Ruka), a Co and/or Mg doped lanthanum chromite interconnection was described. Means of making the interconnection were generally described as including vapor deposition and traditional sintering techniques.

An improved method of bonding fuel cell interconnections was taught in U.S. Pat. No. 4,861,345 (Bowker et al.), where particles of lanthanum chromite, doped with at least one of Sr, Mg, Ca, Ba and Co, and having on each particle surface a coating of $CaO+Cr_2O_3$, were placed on an air electrode surface and heated in air without any applied pressure. The Ca and Cr coated on the surfaces of the individual particles were incorporated into the structure of the lanthanum chromite. This system allowed formation of sintered interconnections without cracking the fragile air electrode by pressure techniques. A slurry of the particles in a $Ca(NO_3)_2+Cr(NO_3)_3$ solution was applied to the air electrode by brushing or tape casting. Heating then formed the layer on the particles. Further heating caused the $CaO+Cr_2O_3$ to melt and flow into voids between the particles and ultimate reduction of void volume in the interconnection. This invention required particle coating, and resulted in a small, open porosity. Even a small open porosity is troublesome for fuel cell operation and life.

What is needed is a convenient method to make lanthanum chromite interconnections without open porosity on air electrodes. It is one of the objects of the invention to provide such a method and to provide such an interconnection on a fuel cell.

SUMMARY OF THE INVENTION

Accordingly, the invention resides in a method of depositing a dense, high temperature electronically conductive interconnection on an electrode structure, characterized by the steps: (1) applying a thin porous, base layer of doped $LaCrO_3$ particles and organic polymer binder on a portion of a first surface of an electrode structure; (2) coating the base layer with a top layer composition selected from the group consisting of $CaO+Al_2O_3$, $SrO+Al_2O_3$, $BaO+Al_2O_3$, $CaO+TiO_2$, $SrO+TiO_2$, $BaO+TiO_2$, and their mixtures; and (3) heating the base layer and the top layer to a temperature and for a time effective to melt the top layer composition and allow it to fill any open pores in the porous base layer of doped $LaCrO_3$.

Preferably, the top layer composition is $CaO+Al_2O_3$ in the form $(CaO)_{12}.(Al_2O_3)_7$, or a mixture of 68 weight % $SrO+32$ weight % $Al_2O_3$, which is $Sr_3Al_2O_6$. The composition is preferably applied in the form of an organic slurry, which organic portion, is removed in part by evaporation and decomposition and in part by oxidation above about 300° C. to 400° C. The electrode structure is an air electrode and is typically but not necessarily, a self-supporting, porous electrode tube of calcium doped $LaMnO_3$.

This method can be used to apply the top layer composition directly to the lanthanum chromite layer followed by heating to sinter the lanthanum chromite layer to the electrode and melt the top layer in one heating cycle. Also, a two step heating process can be used, in which the layer of lanthanum chromite particles is applied and then heated to provide a porous layer of doped lanthanum chromite which is firmly attached to the air electrode structure, then depositing the top layer composition which is melted in the second heating step to densify the lanthanum chromite layer.

The invention also resides in a self-supporting, gas-permeable, electrically conductive air electrode characterized as having on a selected portion thereof a sintered layer of doped $LaCrO_3$, which layer is a solid solution of doped $LaCrO_3$ and a composition selected from the group consisting of $CaO+Al_2O_3$, $SrO+Al_2O_3$, $BaO+Al_2O_3$, $CaO+TiO_2$, $SrO+TiO_2$, $BaO+TiO_2$, and their mixtures; and where the remaining portion of the air electrode tube is covered with solid oxide electrolyte, which electrolyte is substantially covered with a cermet exterior electrode. This provides an electrochemical cell, a plurality of which can be electrically connected together. The electrode can be in tubular or flattened tubular form.

In this invention, various well known application methods can be used to apply the coatings required for these interconnections. For example, tape casting (single or multi-layer), organic slurry coating (single or multi-layer), brush-on, spray-on, other direct-deposition methods and screen-printing are all suitable. The method used can be selected to give the desired degree of automation to reduce cost while maintaining sufficient precision of thickness and edge shape/definition of the applied layers. Also, the processes disclosed in this invention are compatible with, but not limited to, the use of "highly sinterable" lanthanum chromites. In fact, a low cost solid state lanthanum chromite powder was used in work demonstrating both the one-step and two-step processes, where dense interconnections without open porosity were produced.

BRIEF DESCRIPTION OF THE DRAWINGS

In order that the invention can be more clearly understood, conventional embodiments thereof will now be described, by way of example, with reference to the accompanying drawings, in which.

DESCRIPTION OF THE PREFERRED EMBODIMENTS

Figure 1:
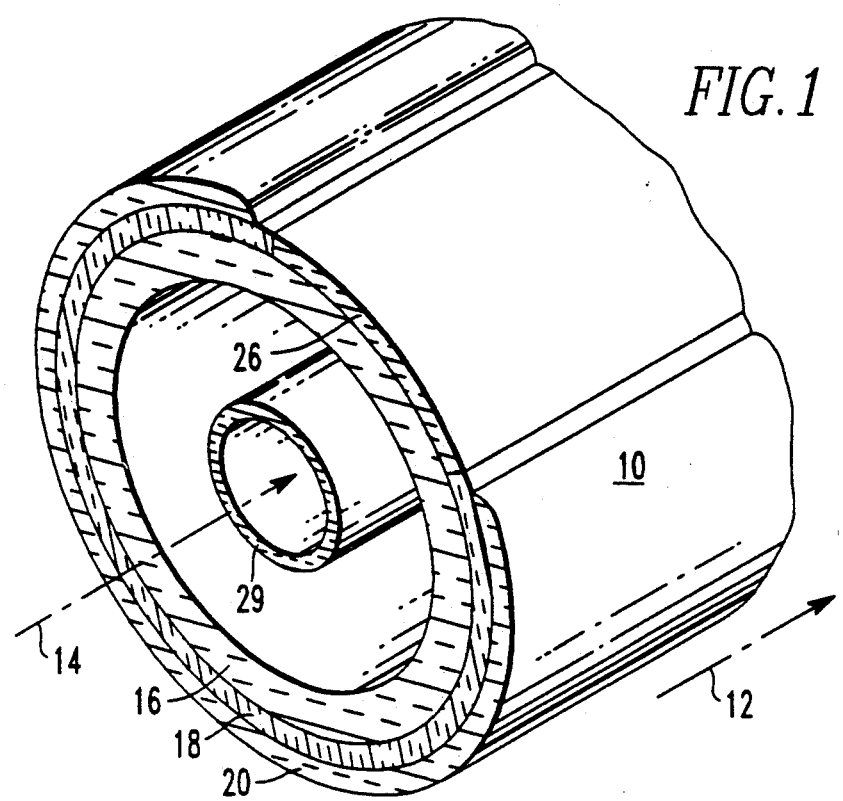
FIG. 1 is a schematic, sectional view of the sintered, doped $LaCrO_3$ interconnection layer of this invention disposed on a self-supporting air electrode layer which supports other components of an electrochemical cell.

Referring now to FIG. 1 of the Drawings, a preferred, tubular, electrochemical cell 10 is shown. The preferred configuration is based upon a fuel cell system, wherein a flowing gaseous fuel, such as hydrogen or carbon monoxide, is directed axially over the outside of the cell, as indicated by the arrow 12, and an oxidant, such as air or $O_2$, indicated by the arrow 14, flows through a feed tube to the end of the cell and then back near the inside wall of the cell. Where the cell is as shown, and operated at a high temperature, oxygen molecules pass through the porous, electronically conductive air electrode structure 16, and are changed to oxygen ions at the air electrode-solid electrolyte interface. The oxygen ions then diffuse through the solid electrolyte 18, to combine with fuel at the fuel electrode 20, which is usually of a cermet (metal-ceramic) construction.

The air electrode, or cathode 16, that is, the electrode which will be in contact with the oxidant (air or oxygen), will, in self-supporting form, have a porous wall approximately 1 millimeter to 3 millimeters thick, preferably from 1 millimeter to 2 millimeters thick. This electrode is preferably a Ca or Sr doped $LaMnO_3$. As seen in FIG. 1, the air electrode structure 16 is thin and of low bulk design. An air feed tube or injector is shown as 29.

The dense interconnection material 26, which preferably extends along a selected portion of the active axial length of each elongated cell 10, on top of the air electrode 16, as shown, must be electrically conductive in both an oxidizing and reducing environment. The gas-tight interconnection 26 generally has a thickness about 30 micrometers to about 100 micrometers (0.03 millimeter to 0.1 millimeter). The interconnection should not have open porosity and must be electronically conductive at 1000° C., the usual operating temperature of the solid oxide electrolyte fuel cell. The usual interconnection material is doped lanthanum chromite ($LaCrO_3$). Dopants for enhancing electrical conductivity can include at least one of Ca, Ba and Sr in the La site, or Mg and Co in the Cr site.

An electrically conductive Ni or Co layer (not shown) can be deposited over part of the interconnection 26. The remaining portion of the air electrode 16, that is, most of the outer periphery of the air electrode 16 is covered by a layer of gas-tight solid electrolyte 18, generally comprised of yttria-stabilized zirconia about 1 micrometer to about 100 micrometers thick (0.001 millimeter to 0.1 millimeter). The electrolyte 18 can be deposited onto the air electrode by well-known, high temperature, electrochemical vapor deposition techniques. A preferred electrolyte composition is $(Y_2O_3)_{0.1}(ZrO_2)_{0.9}$.

The exterior layer is the fuel electrode, or anode 20, which is generally composed of a nickel-zirconia or a cobalt-zirconia cermet, and is about 100 micrometers thick. It covers a substantial portion of the electrolyte 18. A major portion of the fuel electrode is a skeletal extension of the yttria-stabilized zirconia solid electrolyte material. Both electrodes are electrically conductive at high temperature; that is, conductive at the usual 1,000° C. cell-operating temperature.

Figure 2:
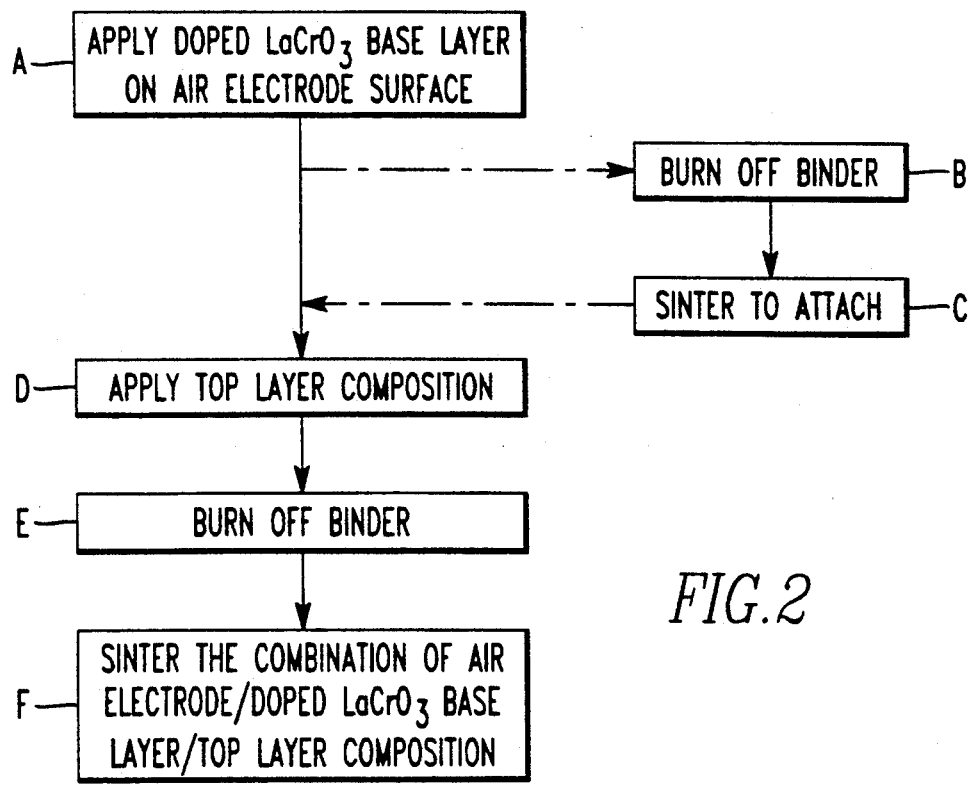
FIG. 2, which best shows the invention, is a schematic drawing of the steps involved in the method of this invention.

In forming the interconnection 26 over a selected portion of the air electrode 16 as shown in FIG. 1, a thin, porous, base layer of doped $LaCrO_3$ can be directly placed on the sintered or unsintered air electrode surface, step A in FIG. 2, by attaching a tape consisting of the lanthanum chromite and organic binder, or by slurry casting a similar layer of the desired dimensions, directly on the air electrode tube surface. This "green" air electrode/interconnection combination is then heated slowly in air to burn off the organic content, optional step B in FIG. 2.

The combination is then further co-fired at a temperature sufficient to firmly attach the doped $LaCrO_3$ interconnection to the air electrode, optional step C in FIG. 2, after which it is cooled to room temperature. This interconnection can be porous to nearly dense at this point. To eliminate the open porosity, a top layer of a second composition, which melts at high temperature and is compatible with lanthanum chromite, is then deposited on top of the base interconnection layer, by tape lamination or slurry casting, step D of FIG. 2. Subsequently, the combination is heated to burn off binder, step E of FIG. 2, then sintered at a temperature sufficient to melt the top layer composition which allows it to close the open porosity, step F of FIG. 2.

The tube can be held at temperature for an additional time to further homogenize and densify the interconnection. The melting top layer must be chemically compatible with the lanthanum chromite interconnection, and after application, the resultant interconnection must be electrically conductive. A calcium-aluminum oxide composition near the composition $(CaO)_{12}(Al_2O_3)_7$ is suitable as the top layer composition. Other materials such as the $SrO+Al_2O_3$ composition of about 32 wt % $Al_2O_3$ and 68 wt % SrO, (that is, $Sr_3Al_2O_6$ or the eutectics at approximately 20 or 24 wt % $Al_2O_3$), $BaO+Al_2O_3$ mixtures such as 76.5 wt % BaO and 23.5 wt % $Al_2O_3$, $CaO+TiO_2$, $SrO+TiO_2$, $BaO+TiO_2$, and their mixtures; and which form melting mixtures compatible with the lanthanum chromite are additional useful materials.

For a one-step co-sintering process, doped lanthanum chromite and a top layer composition similar to those suggested above can be used. In this case, the doped lanthanum chromite base layer can be deposited on the surface of either a "green" or a sintered air electrode tube, step A of FIG. 2; the top layer composition can be applied on the lanthanum chromite base layer, step D of FIG. 2; then the combination of air electrode/doped lanthanum chromite base layer/top layer sealing composition is heated to burn off the binder, step E of FIG.

2; then sintered to form a dense interconnection which is firmly attached to the air electrode surface, step F of FIG. 2. The one-step co-sintering process is desirable because it will lower the manufacturing costs.

Various well known application methods can be used to apply the coatings required for these interconnections. For example, tape casting (single or multi-layer), slurry coating (single or multi-layer), brushon, spray-on, other direct-deposition methods and screen-printing are all suitable. The method used can be selected to give the desired degree of automation to reduce cost while maintaining sufficient precision of thickness and edge shape/definition of the applied layers.

After interconnection application, the interconnection is masked and the remaining portion of the air electrode is unmasked. Then, solid oxide electrolyte is applied, usually by well known chemical/electrochemical vapor deposition techniques on the remaining portion of the air electrode. Finally, the cermet, exterior fuel electrode is coated onto substantially all of the electrolyte surface by electrochemical vapor deposition or sintering techniques.

The invention will now be illustrated with reference to the following non-limiting Example.

EXAMPLE

As an example, we have co-sintered "green" air electrodes of $La_{0.8}Ca_{0.2}MnO_3$ with overlaid Sr-doped lanthanum chromite slurry layers at temperatures between 1500° and 1550° C. to form a porous doped $LaCrO_3$ layer firmly bonded on the air electrode. Typically these layers are made in the range of 20 to 100 micrometers thickness, in a band about 0.5 to 1.0 cm in width. On top of this sintered but porous base layer of doped $LaCrO_3$ we slurry cast a top composition layer of $(CaO)_{12}(Al_2O_3)_7$, heat slowly to remove organic materials in the slurry cast composition, and after about 600° C. heat at about 5° C./min to about 1450° C., hold two hours and cool. This results in a firmly adherent leak-tight interconnection.

The above-mentioned method consisted of two firing steps. However, this process was also done in one co-firing step. In such case, a base lanthanum chromite slurry layer was first deposited on the unfired air electrode surface and then a top slurry layer of $CaO+Al_2O_3$ was deposited on top of the lanthanum chromite layer. This "green" air electrode/lanthanum chromite/$CaO+Al_2O_3$ combination was then heated in one firing cycle to burn off the organic materials below 600° C. and then co-sintered at 1550° C. for 7 hours. The one-step method also resulted in a gas-tight, electrically conductive interconnection.

In both cases, the interconnection was electrically conductive. The resulting interconnection was essentially single phase, with a solid solution of the lanthanum chromite and the melting $CaO+Al_2O_3$ having occurred during the heat treatments.

We claim:

1. A method of depositing a dense, high temperature electronically conductive interconnection on an electrode structure, comprising the steps:
    (a) applying a thin porous, base layer of doped $LaCrO_3$ particles and organic polymer binder on a portion of a first surface of an electrode structure;
    (b) coating the base layer with a top layer composition selected from the group consisting of $CaO+Al_2O_3$, $SrO+Al_2O_3$, $BaO+Al_2O_3$, $CaO+TiO_2$, $SrO+TiO_2$, $BaO+TiO_2$, and their mixtures; and
    (c) heating the base layer and the top layer to a temperature and for a time effective to melt the top layer composition and allow it to fill any open pores in the porous base layer of doped $LaCrO_3$.

2. The method of claim 1, where the $LaCrO_3$ is doped with at least one of Ca, Ba, Sr, Co, and Mg.

3. The method of claim 1, where the electrode is a self supporting, tubular, axially elongated structure comprising Ca or Sr doped $LaMnO_3$, and where, after step (a), the particles and binder are heated to remove the binder and provide a layer of doped $LaCrO_3$ particles, which particles are further heated to firmly attach them to the electrode structure.

4. The method of claim 1, where the $LaCrO_3$ is doped with Sr and Co, and where, after step (b) the $LaCrO_3$ particles and the top layer composition are first heated to sinter the particles to the electrode structure and then to melt the top layer composition.

5. The method of claim 1, where the top layer composition is selected from the group consisting of $(CaO)_{12}(Al_2O_3)_7$ and $Sr_3Al_2O_6$, and where the top layer is applied as an organic based slurry or tape and the doped $LaCrO_3$ particles are applied as an organic based slurry or a tape.

6. Method of claim 1, where a solid oxide electrolyte is applied to the remaining portion of the electrode structure, which electrolyte is then substantially coated with a cermet, exterior electrode to provide an electrochemical cell.

7. The method of claim 6, where a plurality of the electrochemical cells are electrically connected together.

8. A self-supporting, gas-permeable, electrically conductive electrode having on a selected portion thereof a sintered layer of doped $LaCrO_3$, which layer is a solid solution of doped $LaCrO_3$ and a composition selected from the group consisting of $CaO+Al_2O_3$, $SrO+Al_2O_3$, $BaO+Al_2O_3$, $CaO+TiO_2$, $SrO+TiO_2$, $BaO+TiO_2$, and their mixtures; and where the remaining portion of the electrode is covered with solid oxide electrolyte, which electrolyte is substantially covered with a cermet exterior electrode.

9. The electrode of claim 8, where the $LaCrO_3$ is doped with at least one of Ca, Ba, Sr, Co, and Mg, the electrode is a self supporting, axially elongated tube comprising Ca or Sr doped $LaMnO_3$, and the composition in the solid solution is selected from the group consisting of $(CaO)_{12}(Al_2O_3)_7$ and $Sr_3Al_2O_6$.

10. A plurality of the electrodes of claim 8 electrically connected together.

* * * * *